:

US012370302B2

(12) United States Patent
Slaby et al.

(10) Patent No.: US 12,370,302 B2
(45) Date of Patent: Jul. 29, 2025

(54) INFUSION PUMP WITH ACCELEROMETER CONTROLLED SURFACE TEMPERATURE

(71) Applicants: BAXTER INTERNATIONAL INC., Deerfield, IL (US); BAXTER HEALTHCARE SA, Glattpark (CH)

(72) Inventors: Jiri Slaby, Buffalo Grove, IL (US); Slawomir Edward Wojtysiak, McHenry, IL (US)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 283 days.

(21) Appl. No.: 17/325,855

(22) Filed: May 20, 2021

(65) Prior Publication Data
US 2021/0361856 A1 Nov. 25, 2021

Related U.S. Application Data

(60) Provisional application No. 63/028,640, filed on May 22, 2020.

(51) Int. Cl.
A61M 5/142 (2006.01)

(52) U.S. Cl.
CPC ..... *A61M 5/142* (2013.01); *A61M 2205/3368* (2013.01); *A61M 2205/3561* (2013.01);
(Continued)

(58) Field of Classification Search
CPC .... A61M 5/42; A61M 5/142; A61M 5/14244; A61M 2005/14208; A61M 2205/3368;
(Continued)

(56) References Cited

U.S. PATENT DOCUMENTS

2008/0125700 A1\* 5/2008 Moberg ............ A61M 5/14244
604/67
2009/0069784 A1 3/2009 Estes et al.
(Continued)

FOREIGN PATENT DOCUMENTS

CN 107530004 A 1/2018

OTHER PUBLICATIONS

Power Electronics, Design Considerations for Maximum Allowable Temperature as per Safety Standards IEC 60601-1, IEC 60950-1 and IEC61010-1AN-G012, 2019 (Year: 2019).\*

(Continued)

*Primary Examiner* — Michael J Tsai
*Assistant Examiner* — Kathleen Paige Farrell
(74) *Attorney, Agent, or Firm* — K&L Gates LLP

(57) ABSTRACT

An infusion pump includes a housing, a pumping mechanism, an accelerometer configured to detect at least one of pump motion and pump angular orientation, and a temperature control unit. The temperature control unit is configured to receive accelerometer data and determine a pump configuration based on the accelerometer data. The pump configuration may include a contact configuration or a non-contact configuration. The temperature control unit is also configured to establish a threshold housing temperature based on the determined pump configuration. Additionally, the temperature control unit is configured to modify at least one pump feature or function to maintain the housing below the threshold housing temperature.

20 Claims, 8 Drawing Sheets

(52) U.S. Cl.
CPC ............... *A61M 2205/583* (2013.01); *A61M 2205/8237* (2013.01)

(58) Field of Classification Search
CPC ........ A61M 5/16831; A61M 2230/063; A61M 5/14; A61M 2205/52; A61M 2205/8212; A61M 2230/63; A61M 2205/3561; A61M 2205/583; A61M 2205/8237; A61M 2205/18; A61M 2205/3584; A61M 2205/502
See application file for complete search history.

(56) References Cited

U.S. PATENT DOCUMENTS

| | | | |
|---|---|---|---|
| 2012/0150114 A1* | 6/2012 | Krogh ................ | H02J 7/00714 604/151 |
| 2016/0129182 A1 | 5/2016 | Schuster et al. | |
| 2017/0296056 A1* | 10/2017 | Hresko et al. ....... | A61B 5/0015 |
| 2019/0190296 A1* | 6/2019 | Paralikar .............. | A61N 1/3787 |
| 2021/0187223 A1* | 6/2021 | Sing ...................... | A61M 11/02 |

OTHER PUBLICATIONS

European Rule 161(1) and 162 Communication for corresponding European Patent Application No. 21733606.4, dated Jan. 5, 2023.
International Preliminary Report on Patentability for International Patent Application No. PCT/US2021/033395, dated Nov. 17, 2022.
First Office Action for CN Application No. 202180036111.6 dated Mar. 14, 2025.

\* cited by examiner

INFUSION PUMP WITH ACCELEROMETER CONTROLLED SURFACE TEMPERATURE

RELATED APPLICATIONS

This application claims the benefit of and priority to U.S. Provisional Patent Application No. 63/028,640 filed May 22, 2020, entitled "INFUSION PUMP WITH ACCELEROMETER CONTROLLED SURFACE TEMPERATURE", which is incorporated herein by reference in its entirety.

BACKGROUND

The present invention relates to a pump and more particularly to an infusion pump for the delivery of a medication to a patient. Generally, medical patients sometimes require precise delivery of either continuous medication or medication at set periodic intervals. Medical pumps have been developed to provide controlled drug infusion wherein the drug can be administered at a precise rate that keeps the drug concentration within a therapeutic margin and out of an unnecessary or possibly toxic range. Basically, the medical pumps provide appropriate drug delivery to the patient at a controllable rate, which does not require frequent attention.

Medical pumps may facilitate administration of intravenous therapy to patients both in and outside of a clinical setting. Outside a clinical setting, doctors have found that in many instances patients can return to substantially normal lives, provided that they receive periodic or continuous intravenous administration of medication. Among the types of therapies requiring this kind of administration are antibiotic therapy, chemotherapy, pain control therapy, nutritional therapy, and several other types known by those skilled in the art. In many cases, patients receive multiple daily therapies. Certain medical conditions require infusion of drugs in solution over relatively short periods such as from 30 minutes to two hours. These conditions and others have combined to promote the development of increasingly lightweight, portable or ambulatory infusion pumps that can be worn by a patient and are capable of administering a continuous supply of medication at a desired rate, or providing several doses of medication at scheduled intervals.

Configurations of infusion pumps include elastomeric pumps, which squeeze solution from flexible containers, such as balloons, into IV tubing for delivery to the patient. Alternatively, spring-loaded pumps pressurize the solution containers or reservoirs. Certain pump designs utilize cartridges containing flexible compartments that are squeezed by pressure rollers for discharging the solutions. Infusion pumps utilizing syringes are also known wherein a drive mechanism moves a plunger of the syringe to deliver fluid to a patient. Typically, these infusion pumps include a housing adapted to receive a syringe assembly, a drive mechanism adapted to move the syringe plunger, a pump control unit having a variety of operating controls, and a power source for powering the pump including the drive mechanism and controls.

Additionally, some infusion pumps are portable, for example, an infusion pump may be smaller and more compact for mobile use by ambulatory patients or other patients. Naturally, a portable pump must be supplied with an equally portable power source as a means for powering the pump motor. Batteries are a suitable choice of power for portable units. Some pumps may use disposable batteries while other pumps may use rechargeable batteries. The pump may also be sized to be attached to an I.V. pole. The I.V. pole, with attached pump, may remain stationary or may be moved about in a hospital setting. In another example, the pump may be attached to a hospital bed or other support structure. As noted above, the pump may be portable and may be carried on the patient, for example, in a pouch. The pump may be attached to and supported by the patient's clothing and/or other support apparel such as a belt, a vest or the like.

While the pumps are operating, the power provided by the power source, such as a battery may dissipate energy and heat up pump components and the pump housing. High pump surface temperatures may cause discomfort to a patient. Multiple needs accordingly exist for patient comfort including one that addresses pump surface temperatures while also maintaining safe pump operation.

SUMMARY

The instant invention provides for an infusion pump with an accelerometer dictated surface temperature. The pump includes an accelerometer, which may be used in conjunction with a variety of other sensors to determine whether the pump is in an ambulatory configuration or a non-ambulatory configuration. Based on the determination of the pump state (e.g., ambulatory vs. non-ambulatory), the power consumption and thus the power dissipation of the pump may be adjusted to limit the surface temperature of the pump to a specified threshold.

Aspects of the subject matter described herein may be useful alone or in combination with one or more other aspects described herein. In an exemplary aspect of the present disclosure, an infusion pump includes a housing, a pumping mechanism, an accelerometer configured to detect at least one of pump motion and pump angular orientation, and a temperature control unit. The temperature control unit is configured to receive accelerometer data and determine a pump configuration based on the accelerometer data. The pump configuration may include a contact configuration or a non-contact configuration. The temperature control unit is also configured to establish a threshold housing temperature based on the determined pump configuration. Additionally, the temperature control unit is configured to modify at least one pump feature or function to maintain the housing below the threshold housing temperature.

In accordance with another exemplary aspect of the present disclosure, which may be used in combination with any one or more of the preceding aspects, the infusion pump further includes an accelerometer.

In accordance with another exemplary aspect of the present disclosure, which may be used in combination with any one or more of the preceding aspects, the accelerometer is configured to detect an orientation of the pump.

In accordance with another exemplary aspect of the present disclosure, which may be used in combination with any one or more of the preceding aspects, the accelerometer is configured to detect an acceleration (e.g., rate of change of velocity) of the pump.

In accordance with another exemplary aspect of the present disclosure, which may be used in combination with any one or more of the preceding aspects, the accelerometer is configured to provide an accelerometer "signature" of the pump to distinguish between pump states (e.g., ambulatory vs. non-ambulatory).

In accordance with another exemplary aspect of the present disclosure, which may be used in combination with any one or more of the preceding aspects, the infusion pump further includes one or more temperature sensors.

In accordance with another exemplary aspect of the present disclosure, which may be used in combination with any one or more of the preceding aspects, the temperature control unit is further configured to receive temperature data from the temperature sensor.

In accordance with another exemplary aspect of the present disclosure, which may be used in combination with any one or more of the preceding aspects, the temperature control unit is further configured to dynamically modify at least one pump feature based on feedback from the temperature data.

In accordance with another exemplary aspect of the present disclosure, which may be used in combination with any one or more of the preceding aspects, the contact configuration is an ambulatory configuration.

In accordance with another exemplary aspect of the present disclosure, which may be used in combination with any one or more of the preceding aspects, the non-contact configuration is a non-ambulatory configuration.

In accordance with another exemplary aspect of the present disclosure, which may be used in combination with any one or more of the preceding aspects, the pump is an ambulatory infusion pump.

In accordance with another exemplary aspect of the present disclosure, which may be used in combination with any one or more of the preceding aspects, the infusion pump is connected to an I.V. pole when in the non-contact configuration.

In accordance with another exemplary aspect of the present disclosure, which may be used in combination with any one or more of the preceding aspects, the at least one pump feature or function includes pump communication settings, battery charging, display settings, sound settings, alert settings, and WiFi communication frequency.

Aspects of the subject matter described herein may be useful alone or in combination with one or more other aspects described herein. In an exemplary aspect of the present disclosure, a method includes monitoring accelerometer data and determining a pump configuration based on the accelerometer data. The pump configuration includes one of a contact configuration and a non-contact configuration. The method also includes modifying at least one pump feature or function to maintain a pump housing below a threshold housing temperature. The threshold housing temperature is based on the pump configuration.

In accordance with another exemplary aspect of the present disclosure, which may be used in combination with any one or more of the preceding aspects, the method further includes setting the threshold housing temperature.

In accordance with another exemplary aspect of the present disclosure, which may be used in combination with any one or more of the preceding aspects, determining the pump configuration includes comparing the accelerometer data to a pre-established pump profile (e.g., a profile determined based on characterization of the pump's accelerometer response under a specific condition or scenario, such as stationary or varied movement conditions).

In accordance with another exemplary aspect of the present disclosure, which may be used in combination with any one or more of the preceding aspects, determining the pump configuration includes comparing the accelerometer data to an instantaneous threshold value.

In accordance with another exemplary aspect of the present disclosure, which may be used in combination with any one or more of the preceding aspects, determining the pump configuration includes comparing the accelerometer data to a cumulative threshold value.

In accordance with another exemplary aspect of the present disclosure, which may be used in combination with any one or more of the preceding aspects, determining the pump configuration includes applying the accelerometer data to a configuration prediction function.

In accordance with another exemplary aspect of the present disclosure, which may be used in combination with any one or more of the preceding aspects, the at least one pump feature or function includes pump communication settings, battery charging, display settings, sound settings, alert settings, and WiFi communication frequency.

Aspects of the subject matter described herein may be useful alone or in combination with one or more other aspects described herein. In an exemplary aspect of the present disclosure, a method includes detecting at least one of a device motion and a device orientation, determining a device configuration based on at least one of the device motion and the device orientation, and adjusting device processes based on the determined device configuration.

In accordance with another exemplary aspect of the present disclosure, which may be used in combination with any one or more of the preceding aspects, the device is an infusion pump.

In accordance with another exemplary aspect of the present disclosure, which may be used in combination with any one or more of the preceding aspects, the infusion pump is an ambulatory infusion pump.

In accordance with another exemplary aspect of the present disclosure, which may be used in combination with any one or more of the preceding aspects, adjusting device processes includes at least one of adjusting device communication settings, adjusting battery recharge rate, adjusting display brightness, adjusting display time-out, adjusting speaker settings, adjusting alert frequency, and adjusting WiFi communication frequency.

Therefore, it is a primary object of the invention to provide for an infusion pump with an accelerometer and control circuitry that is capable of determining the pump configuration (e.g., ambulatory configuration vs. non-ambulatory configuration).

Additional features and advantages of the disclosed infusion pump are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein. Moreover, it should be noted that the language used in the specification has been principally selected for readability and instructional purposes, and not to limit the scope of the inventive subject matter.

DETAILED DESCRIPTION OF EXAMPLE EMBODIMENTS

The below disclosure relates to an infusion delivery system, such as an infusion pump 110, which is used to deliver fluids (e.g., medications or nutrients) to a patient in predetermined quantities. The infusion pump 110 may be used in a non-ambulatory configuration (illustrated in FIG. 1A) or in an ambulatory configuration (illustrated in FIG. 1B).

Figure 1A:
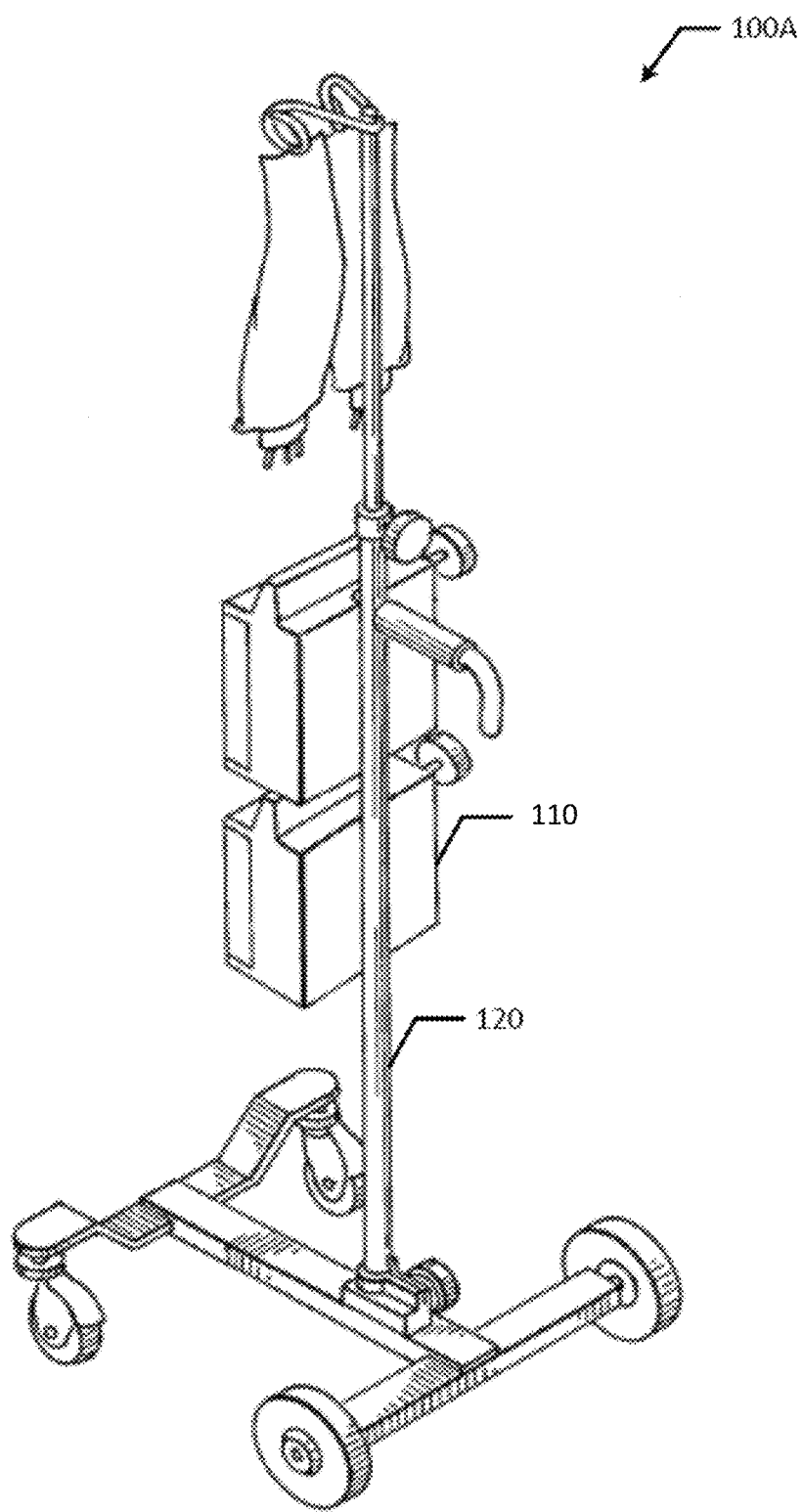
FIG. 1A is a perspective view of an infusion pump in a non-ambulatory configuration according to an example embodiment of the present disclosure.

In the non-ambulatory configuration (e.g., a non-contact configuration) illustrated in FIG. 1A, the pump 110 may be sized and shaped to be attached to a pole assembly 120 (e.g., an I.V. pole). For example, pump 110 may be attached to a pole assembly via a pole clamp, which is adapted to mount the pump 110 to the pole assembly 120 (e.g., pole assembly used in a hospital setting). In operation and in a non-ambulatory configuration, the pump 110 may be mounted on a support structure such as a pole such that it is away from and not in direct contact with a patient.

Typically, two scenarios exist for the non-ambulatory (e.g., non-contact) configuration including hospital use and at home use with a pump in a stationary location. The pump's surface temperature limit is higher in the non-ambulatory configuration. Depending on material and contact time, the surface temperature may be as high as 71° C. for a 1-second touch on plastic material. The 71° C. surface temperature is higher than the ambulatory use case because the device is positioned on a pole 120 rather than on the patient's body. The surface temperature limits may be defined by use case, material to be touched (plastic, metal, etc.), and duration of the touch. For example, the surface temperature limits may be established by a standards body. The surface temperature limits may define acceptable maximum temperatures for various materials based on touch times. Example surface temperature limits are described in "Tables 23—Allowable Maximum Temperatures for ME EQUIPMENT Parts That are Likely to be Touched" and "Table 24—Allowable Maximum Temperatures for Skin Contact With ME EQUIPMENT APPLIED PARTS" per IEC60601-1, $3^{rd}$ edition, which are incorporated herein by reference.

Figure 1B:
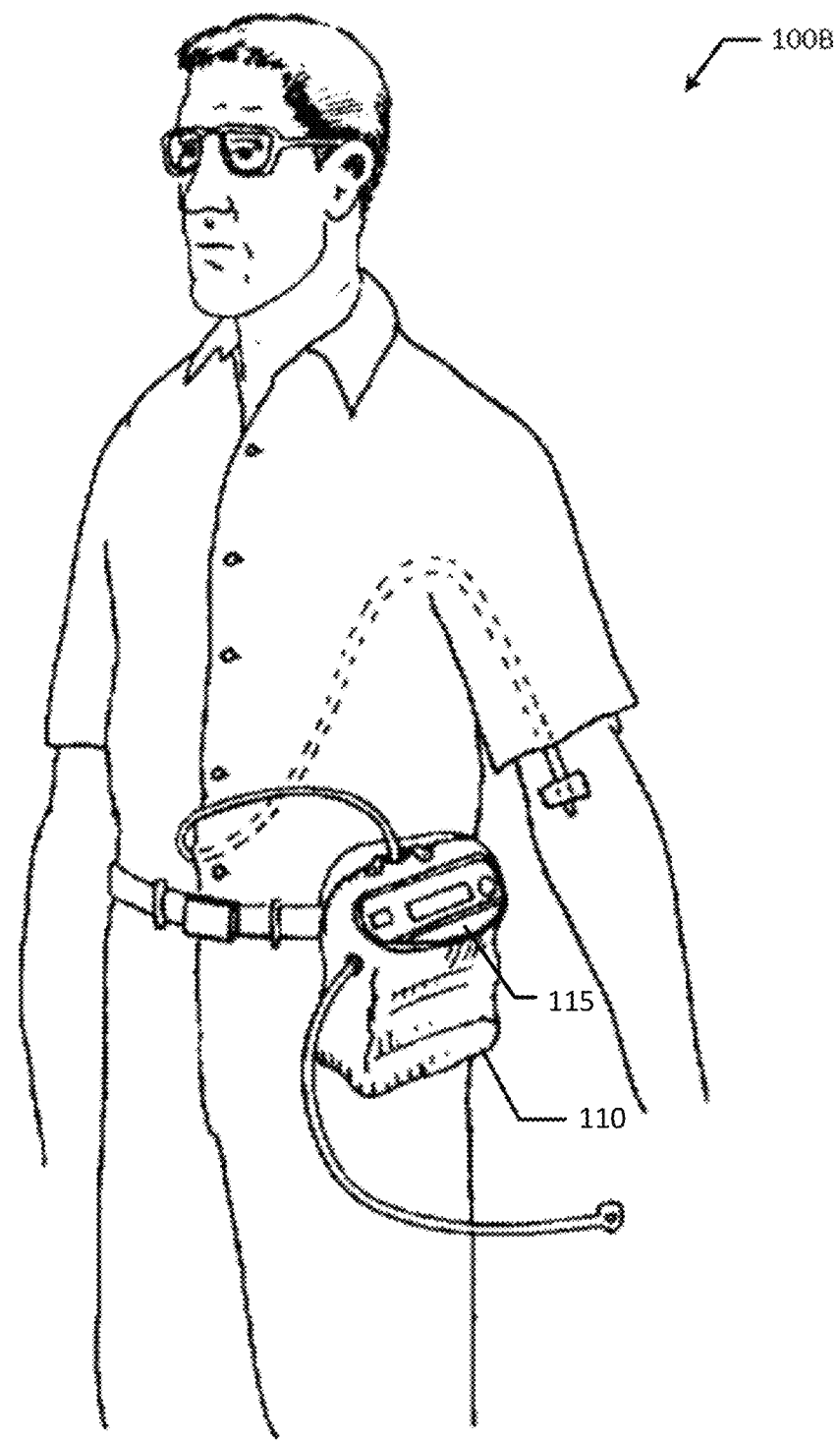
FIG. 1B is a perspective views of an infusion pump in an ambulatory configuration according to an example embodiment of the present disclosure.

In the ambulatory configuration illustrated in FIG. 1B, the pump 110 may be attached to a patient such that the pump housing 115 is in direct contact with the patient's skin or the patient's clothing or through carrying pouch. Typically, two scenarios exist for the ambulatory (e.g., contact) configuration including home use on a patient and hospital use on a patient. In the ambulatory configuration, the patient wears or carries pump 110, which may be in direct contact with the patient's body. Therefore, the surface temperature may be limited to as low as 48° C. regardless of material. As mentioned above, the surface temperature may be limited based on and established standard that describes surface temperature limits based on materials and expected touch times. Regardless of the configuration, the pump 110 may include a housing 115, a door pivotally connected to the housing, a display, and a keypad, etc. The display and the keypad may be used to program the infusion pump 110, and more specifically, a processor in the pump to set the fluid delivery amount, etc., which is later communicated to the pumping mechanism. It should be appreciated that in various other embodiments, one or more elements of the display and the keypad could be combined at a central touch screen.

The housing 115 may be made from a variety of materials including various types of plastics and metals. As discussed above, depending on the configuration (e.g., ambulatory or non-ambulatory) and the material of the housing, the pump 110 may have different surface temperature compliance limits. For example, the surface temperature compliance limits differ depending on duration of exposure (e.g., touch) to a body and the pump housing material. There is a need for the device to recognize the pump configuration (e.g., ambulatory or non-ambulatory) to adjust the internal processes to reduce the power dissipation, when necessary, to maintain the surface temperature of the pump housing below an established compliance limit. In ambulatory use cases or configurations, a temperature above the compliance limit or threshold may cause discomfort or injury to a patient. In the example devices and methods disclosed herein, the pump 110 is configured to maximize patient's comfort and mobility without sacrificing quality of care. Similarly, there is a need to maximize the performance when the medical device is used for non-ambulatory purposes. In the example devices and methods disclosed herein, the pump 110 is configured to maximize pump performance in accordance with the higher temperature compliance limits for pumps used in a non-ambulatory configuration (e.g., positioned on a pole assembly 120 in a non-contact configuration).

Figure 2:
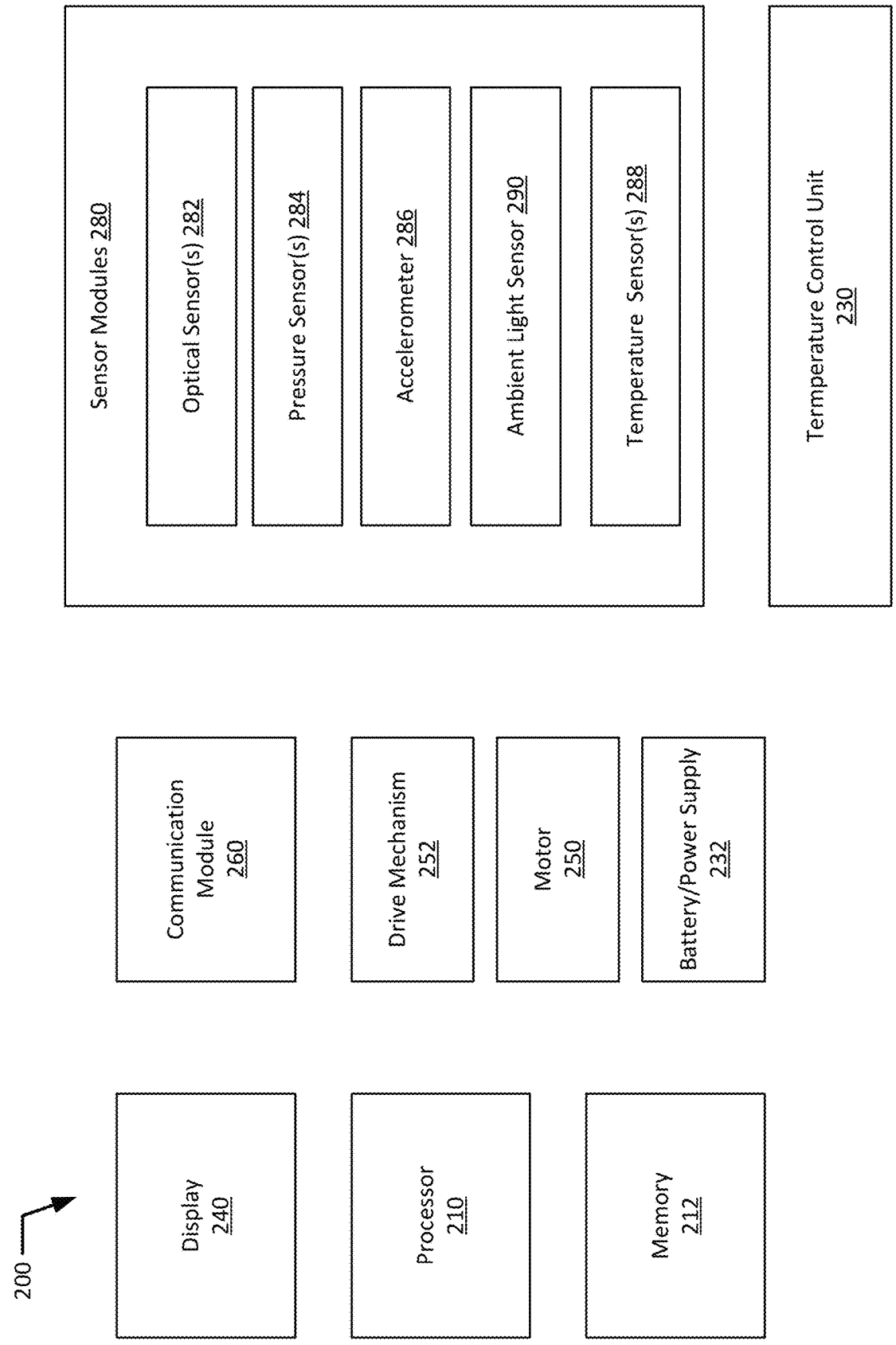
FIG. 2 illustrates a block diagram of an example infusion pump system according to an example embodiment of the present disclosure.

FIG. 2 depicts a high-level component diagram of an infusion pump system. The infusion pump system 200 includes a processor 210 in communication with memory 212, and a temperature control unit 230, which is powered by a battery or power supply 230. The processor 210 communicates with a display 240, a motor 250 and associated pumping mechanism or drive mechanism 252, and a communication module 260. Additionally, the infusion pump system 200 may include various sensor modules 280, such as optical sensor(s) 282, pressure sensor(s) 284, an accelerometer(s) 286, temperature sensors(s) 288, and/or an ambient light sensor 290.

The sensors associated with the pump 110 are operative to provide information as to the pump's function, the pump's location, the pump's temperature (e.g., pump housing surface temperature), and the pump's operational state. In an example, the sensor(s) may obtain data indicative of an external pump housing temperature, a corresponding time period associated with a respective pump housing temperature, and accelerometer data corresponding to forces experienced by a component (e.g., housing) of the infusion pump 110. For example, the temperature sensor(s) (e.g., a thermistor or thermocouple) may be adapted to sense the temperature of the pump housing (or a temperature that is at least representative thereof); i.e., the housing temperature may be characterized to thermistor temperatures.

The power supply 230 may take many different forms. In one preferred embodiment, the power supply 230 may be in the form of a rechargeable battery unit. Additionally, the pump may be powered from an AC power supply. The AC power supply assembly has a power cord and an associated terminal that plugs into the housing. The AC power supply assembly has a plug that can be inserted into a standard electrical outlet to recharge the rechargeable battery when necessary. The AC power can also be supplied through the assembly to power the pump.

Accelerometer

Figure 4:
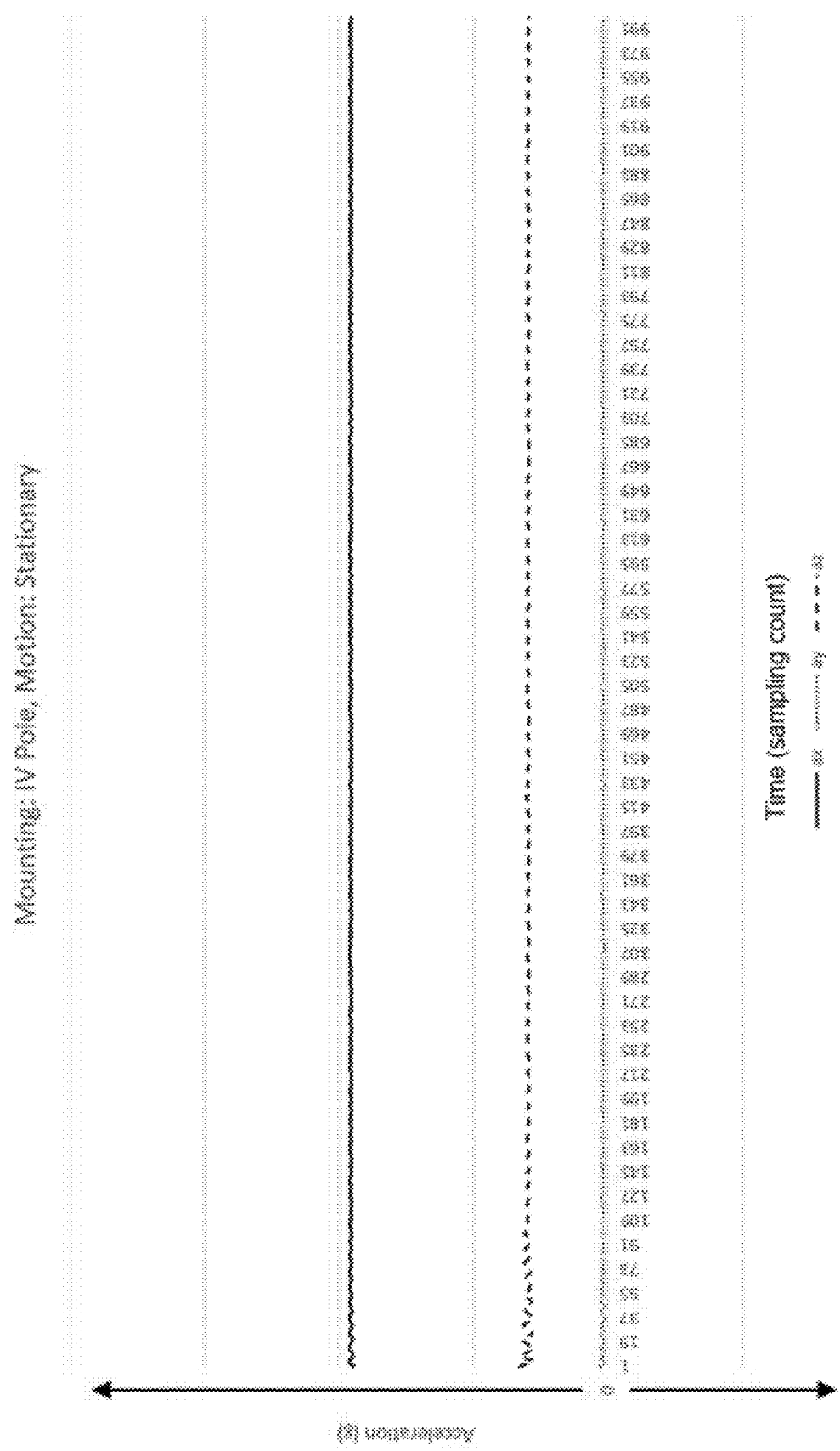
FIG. 4 illustrates accelerometer readings of a pump in a non-ambulatory configuration according to an example embodiment of the present disclosure.
Figure 5:
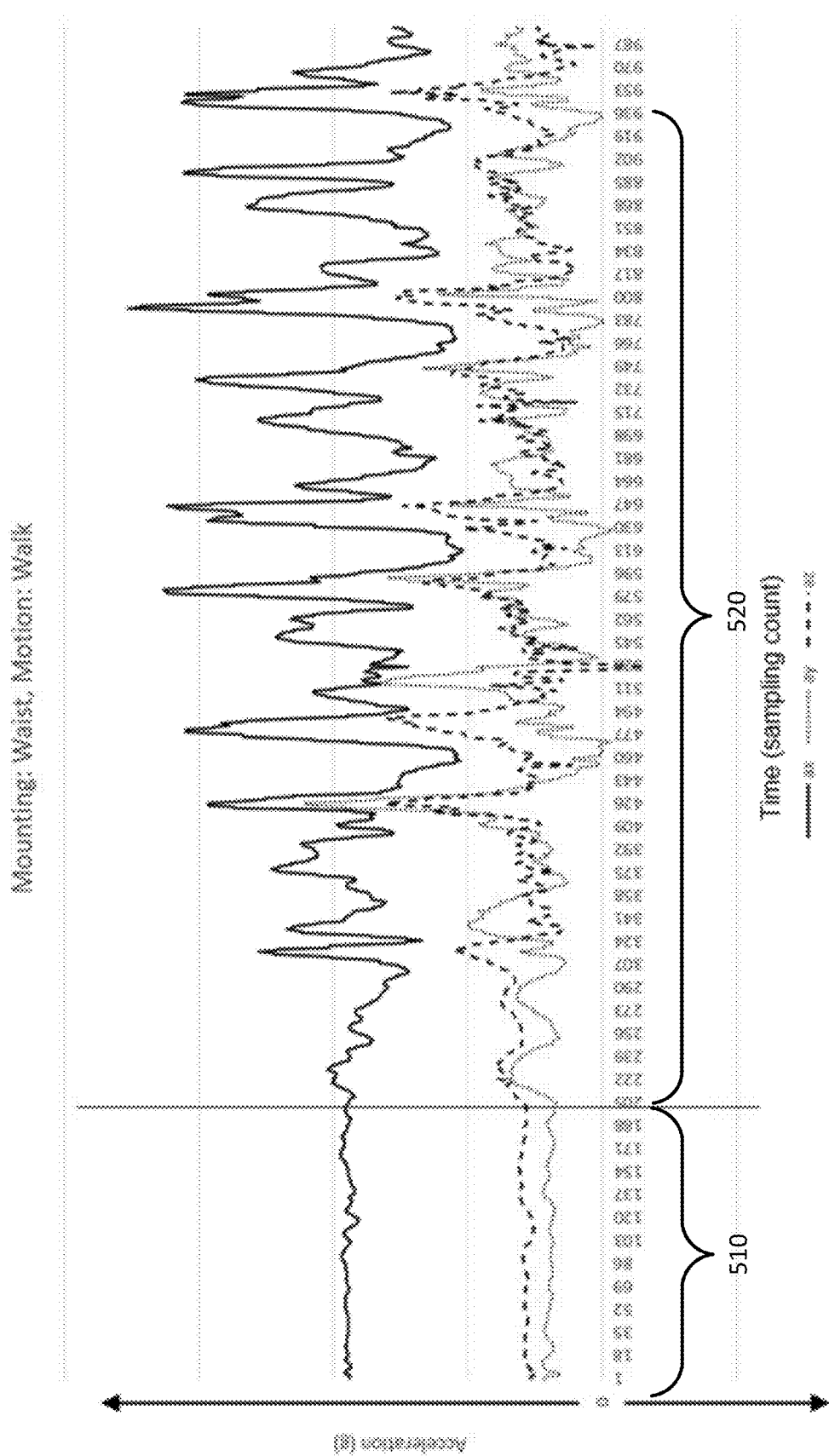
FIG. 5 illustrates accelerometer readings of a pump in an ambulatory configuration according to an example embodiment of the present disclosure.

The accelerometer may sense and measure acceleration (rate of change of velocity) of a body in its own instantaneous rest frame. Specifically, the accelerometer may sense and measure acceleration data (e.g., "g-values") of the pump in the x-direction, y-direction, and z-direction. The accelerometer in the pump may be used to detect ambulatory vs. non-ambulatory configurations or use cases based on an accelerometer behavior "signature". For example, each configuration or use case may provide a unique accelerometer signature based on the device's motion (or lack thereof) and/or the device's angular orientation. For example, as illustrated in FIG. 4 and FIG. 5, the accelerometer may provide the g-values for the x, y and z directions at a sample frequency. Different sampling frequencies may be used based on the application of the pump and to optimize the pump's ability to determine whether the pump is in an ambulatory configuration or a non-ambulatory configuration and adjust the power dissipation of the pump while conserving battery power.

As discussed above, the accelerometer may be used to help distinguish which orientation or configuration the pump 110 is in (e.g., ambulatory vs. non-ambulatory). The accelerometer data may be averaged over a period of time to reduce noise. In an alternative embodiment, digital moving average filters may be used to filter out unwanted spikes and/or noise signals. For example, the pump 110 may generate its own mechanically generated noise or external events may generate noise, which may be filtered from the data. Example sources of such noise may be from an operator pushing on the door of the infusion pump, an operator bumping into the pump, an operator moving the pump (e.g., pump connected to a mobile I.V. pole 120), and patient while infusing, etc.

In an example, if the accelerometer detects movements above a certain detection criteria (e.g., above an instantaneous threshold, above a cumulative threshold, according to a configuration prediction function), the pump 110 may be classified as being in the ambulatory configuration. A threshold may be established for an I.V. pole rolling over, an elevator entrance, etc. Similarly, if the accelerometer detects movements below the detection criteria, the pump 110 may be classified as being in the non-ambulatory configuration.

For example, the configuration prediction algorithm may ensure that the pump 110 is properly classified such that the appropriate threshold for the pump's external housing temperature may be established. With an accelerometer sensitive enough to detect small movements/vibrations, the ambulatory configuration can be accurately detected even when the patient is stationary because even when the patient's body is "stationary", motions are still recorded by the accelerometer (e.g., body is never completely still due to breathing, heartbeat, etc.). For example, small movements and vibrations are indicated by the accelerometer data illustrated in FIG. 4 while FIG. 5 illustrates accelerometer data associated with movements or vibrations associated with increased activity (e.g., walking).

Temperature Control Unit

The pump 110 may also include a controller, such as a temperature control unit 230. Temperature information from the temperature sensor may be provided to the controller, temperature control unit 230 or processor, to modify pump parameters and pump functions to change the power dissipation of the pump 110. The ability to distinguish the two pump states (ambulatory vs. non-ambulatory) then allows the temperature control unit 230 to determine which device components to target for temperature control, and hence, which processes to modify, adjust, reduce, disable, etc. and how to modify those pump processes. For example, the temperature control unit 230 may modulate the battery recharging process as a function of temperature as is described below, or the temperature control unit 230 may adjust display and keypad backlight(s), wireless transmission frequency, etc.

The temperature control unit 230 may include control circuitry in communication with the power supply such as the battery and/or a power line adapter, and the temperature sensor. Other than controlling the temperature of the pump housing, the temperature control unit 230 may be used to provide an alarm if the pump housing temperature exceeds a specified threshold limit.

In some embodiments, the temperature control unit 230 includes a timer or a clock relay to control power settings on the pump for certain time intervals. In other embodiments, the pump housing temperature may be adjusted based on a temperature control signal received from the temperature control unit 230 and/or temperature sensor, thereby providing feedback information to dynamically change pump settings in addition to standard settings established for a specific pump configuration (e.g., ambulatory or non-ambulatory). The feedback control based on the temperature control signal may advantageously provide additional flexibility with the pump control to account for variation in the ambient temperature of the environment, level of activity of the patient, etc. In some examples, other temperature sensors may communicate with the pump to provide the pump information about the ambient temperature (e.g., room temperature or outside temperature) to further refine decisions of how to modify pump parameters and pump functions to prevent the pump housing from exceeding a predetermined threshold temperature. For example, external sensors may send signals to the temperature control unit 230, for example via wireless transmissions carried out using WiFi or other RF technologies, such as Bluetooth®. Alternatively, a local home network may be used for transmitting the temperature control signal through a smart thermostat.

Power Management—Battery

The temperature control unit 230 may provide dynamic power and heat management for the infusion pump. The power and heat management may be based on the configuration of the pump 110 (e.g., ambulatory vs. non-ambulatory). Additionally, the power and heat management may additionally be based on medication criticality that the pump is delivering. For example, a pump that is delivering a highly critical medication may be allocated more power so that the battery is charged to a level that reduces risk to the patient from a depleted battery after AC has been removed.

The temperature control unit 230 may adjust power consumption by changing settings of the following pump functions or features: pump communication, battery charging, display (e.g., brightness and time-out), sounds and alerts, USB, WiFi communication frequency such as limiting uploads and downloads to every five minutes or every two minutes instead of every 30 seconds, CPU rate, CPU loading, etc. For example, when in an ambulatory configuration, the display may be limited to a maximum brightness setting that is less than 50% brightness to reduce power consumption and therefore power dissipation. Similarly, for ambulatory configurations, the pump 110 may have a quicker display timeout to reduce the amount of power consumed by the display. The temperature control unit 230 may also manage power based on medication criticality and may also manage motor consumption per medication needs.

For example, the temperature control unit 230 may implement several methods or procedures to control battery consumption and charging of the infusion pump. The temperature control unit 230 may also manage the amount of power that a pump is using for things other than battery charging, such as driving its motor.

The temperature control unit 230 may allow a pump power supply or wall wart to draw higher current for faster charging when positioned in a non-ambulatory configuration where higher surface temperatures are acceptable. The temperature control unit 230 may also detect failure modes, such as exceeding thermal constraints based on readings from one or more sensor(s) (e.g., accelerometer, temperature sensor, etc.).

As described above, the temperature control unit 230 may adjust how much power the battery is capable of supplying to the pump 110 as a function of pump configuration and/or pump temperature. Additionally, the temperature control unit 230 may modulate the battery recharging process as a function of pump configuration and/or pump temperature. Heat from the battery can increase the temperature of the pump housing during use and during recharging, especially during rapid recharging.

The recharging process of the pump battery may be controlled by circuitry associated with or in communication with the temperature control unit 230. Based on the configuration of the pump 110 and the established surface temperature limits for the respective configuration, the temperature control unit 230 may adjust the recharge rate of the battery as a function of at least one of the pump configuration, the temperature sensed by temperature sensor, and the threshold surface temperature. The recharge rate may be determined to both advantageously recharge the battery rapidly while also avoiding reaching or exceeding the threshold surface temperature. In an example, the recharge rate may be modulated or dynamically adjusted as the pump housing approaches the threshold temperature to allow for quick recharging while the temperature of the pump housing is within safe limits. Modulation of the recharging process may be accomplished by selectively increasing or decreasing the recharge rate of the battery (e.g., by controlling current), for example as a function of sensed temperature. The temperature control unit 230 may be configured to maintain the sensed temperature within a temperature range that is below a predetermined maximum for the pump housing.

In an example, the threshold temperature is 71° C. while the pump is positioned in a non-ambulatory or non-contact configuration (e.g., when positioned on an I.V. pole 120) and the threshold temperature is 48° C. while the pump is positioned in an ambulatory or contact configuration.

Alarms

The pump 110 may be configured such that the alarm will be activated when a temperature of the housing exceeds a predetermined temperature. For example, the temperature control unit 230 may initiate an alert or an alarm when the pump exceeds the predetermined temperature or as the pump 110 nears the predetermined temperature. In some embodiments, the pump 110 may include a cooling element or a fan to reduce to the surface temperature of the housing should the housing exceed a specified threshold condition.

Auxiliary Inputs

In other examples, auxiliary information may be collected and used alone or in combination with the accelerometer data to enhance or refine the selection of ambulatory vs. non-ambulatory configurations or use cases. Additionally, the auxiliary information may assist with power and heat management decisions. For example, auxiliary information may be gathered from sensors integrated into the medical device (e.g., pump 110), which may include multisensory inputs from a gyroscope, eCompass, etc. These inputs may be used to further refine the pump configuration detection process. Other information obtained from the pump 110 may include what power source the pump 110 is currently using (e.g., battery or power cord) and whether the pump is in a battery charging state (e.g., charging vs. not charging). The medical device (e.g., pump 110) may also provide information regarding the battery type (e.g., disposable AA batteries, rechargeable Li-Ion battery, etc.). The type of power source, the battery charging state, and the type of batteries may affect the surface temperature profile of the pump 110 and gathering the auxiliary information may improve power and heat management of the pump 110.

Other auxiliary information may be gathered from the medical device (e.g., pump 110), a mobile device, an Internet of Things ("IoT") device linked to the medical device (e.g., pump 110), or an IoT device linked to the mobile device that is linked to the medical device (e.g., pump 110). The auxiliary information from any one of the above devices may include distance information from and IR distance sensor that detects the nearest object from the front of the medical device (e.g., pump 110). Presence sensors may be used to determine the location of the pump 110, for example, a pole clamp presence sensor may detect if the pump 110 is positioned on a pole clamp (indicating that the patient is likely inside and stationary). The devices above may also detect or sense sound information from the environment.

Additionally, the auxiliary information from any one of the above devices may include location information (e.g., GPS, WiFi, Bluetooth, or manually entered location information). More specifically, certain WiFi networks may be tracked to improve confidence over time that proximity of certain networks likely results in ambulatory or non-ambulatory pump state. For example, some network SSIDs may be associated with a certain pump state. Additionally, the devices above (e.g., sensors on the devices) may provide ambient light information including the variability and wavelength of the ambient light, whether the ambient light is UV light, natural light or artificial light. The ambient light information may be used when determining display brightness and time-out. Similarly, the devices may provide ambient temperature information, which may indicate if there is minimal variances in ambient temperatures (e.g., the patient is indoors) or if there are broad variances in ambient temperatures (e.g., the patient is outdoors and/or moving). Humidity information may also be gathered and may be used to determine if the pump 110 is indoors or outdoors. Other information may include the presence of particulate matter, air quality, time of day, etc.

As noted above, the auxiliary information may be collected and used alone or in combination with the accelerometer data for power and heat management decisions. For example, different surface temperature targets may be used for hospital use and at-home use. Additionally, information regarding whether a battery is used or if the pump is plugged in and a power adapter is used may also affect the power state or power mode the pump 110 is placed in example, if the pump 110 is using battery power, a lower power mode may be used while a higher power mode may be used while the pump is plugged in. Additionally, if the accelerometer or other sensor data indicates that the pump 110 is in an ambulatory configuration, the pump 110 may be placed in a lower power mode. Conversely, if the pump 110 is in a non-ambulatory configuration, the pump 110 may be placed in a higher power mode.

Sample Data

Figure 3:
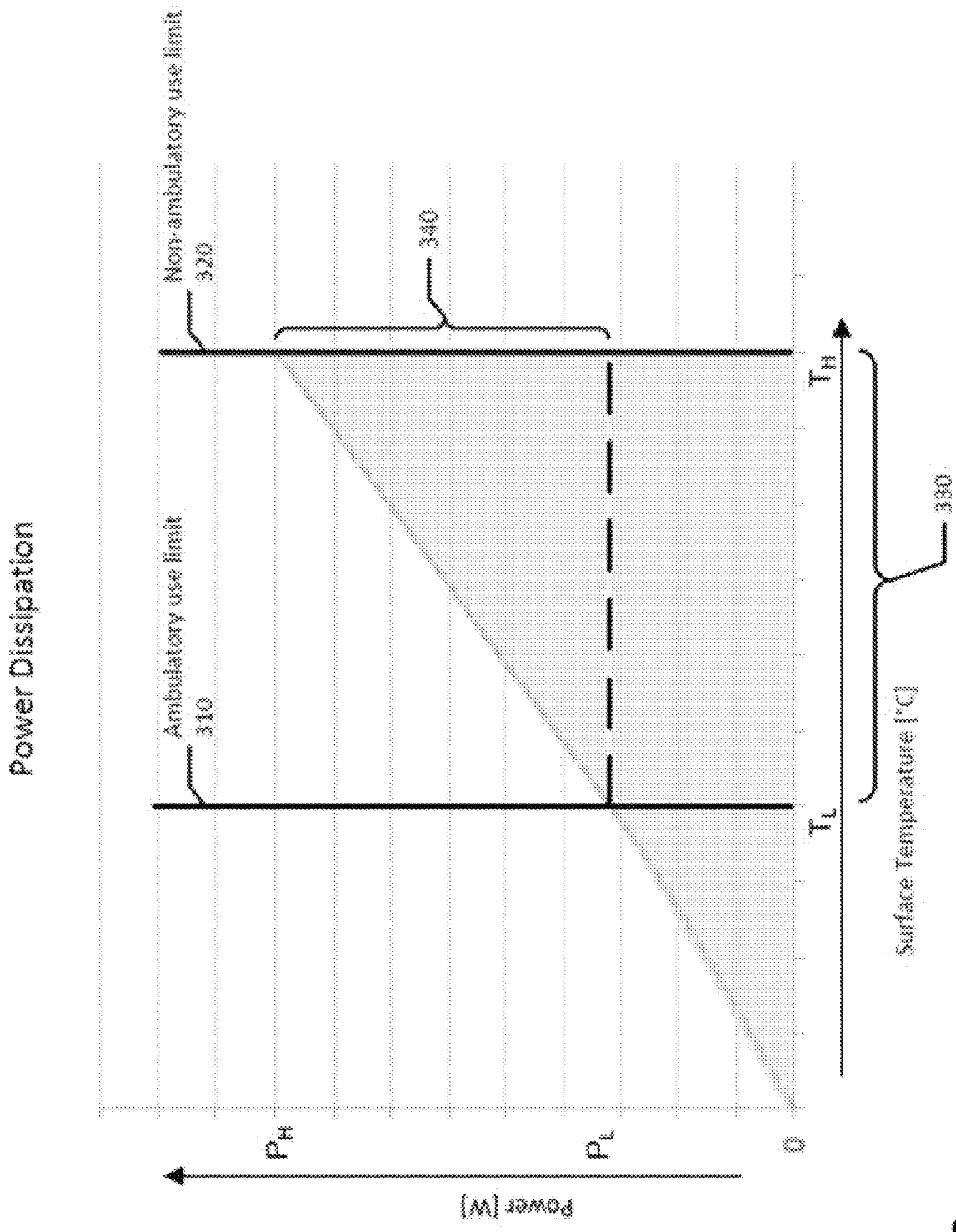
FIG. 3 illustrates a power dissipation graph of power plotted against surface temperature according to an example embodiment of the present disclosure.

As illustrated in FIG. 3, the power or power dissipation is plotted against surface temperature. A pump 110 may use more power with higher surface temperature limits. The surface temperature limit for the pump 110 may be established based on the pump configuration or use case (e.g., ambulatory vs. non-ambulatory). In the illustrated example, the surface temperature limit 320 may be set to $T_H$ for a non-ambulatory temperature limit 320. Additionally, the surface temperature limit 310 may be set to $T_L$ for an ambulatory temperature limit 310. For example, as illustrated in FIG. 3, a surface temperature limit of $T_H$ allows the pump 110 to use $P_H$ Watts of power. On the other hand, a surface temperature limit of $T_L$ restricts the pump to use approximately $P_H$ Watts of power, which is approximately three times lower power dissipation. The power difference 340 (e.g., approximately $P_H$–$P_L$ Watts) between each temperature limit 310, 320 allows a pump 110 in a non-ambulatory use case to fully utilize various pump features. Using each of the pump features to maximize performance and functionality may increase the power dissipation above $P_L$ Watts and thus increase the surface temperature above $T_L$, which would otherwise be unacceptable if the pump 110 were used in an ambulatory configuration.

FIG. 4 illustrates accelerometer readings of a pump in a non-ambulatory configuration 100A according to an example embodiment of the present disclosure. As illustrated in FIG. 4, the accelerometer readings (e.g., "g-values") are relatively flat for the pump 110 in the x-direction, y-direction and z-direction. The resulting vector of the three "g-values" may be used to determine the angular orientation of the pump in relation to the direction of gravity. The accelerometer readings illustrated in FIG. 4 may represent an angular orientation of a pump on a pole mount (e.g., an angular orientation of approximately 10-20 degrees in relation to the direction of gravity). The accelerometer behavior signature for the non-ambulatory or non-contact configuration is indicative of the pump's lack of motion and the pump's constant angular orientation.

FIG. 5 illustrates accelerometer readings of a pump 110 in an ambulatory configuration 100B according to an example embodiment of the present disclosure. As illustrated in region 510 of FIG. 5, the accelerometer readings (e.g., "g-values") are relatively flat when the patient is stationary, but still show significant differences compared to the readings illustrated in FIG. 4. The accelerometer behavior signature for the ambulatory or contact configuration is even more pronounced in region 520 when the patient is moving, which is indicative of the pump's motion and the pump's changing angular orientation.

Methods

Figure 6:
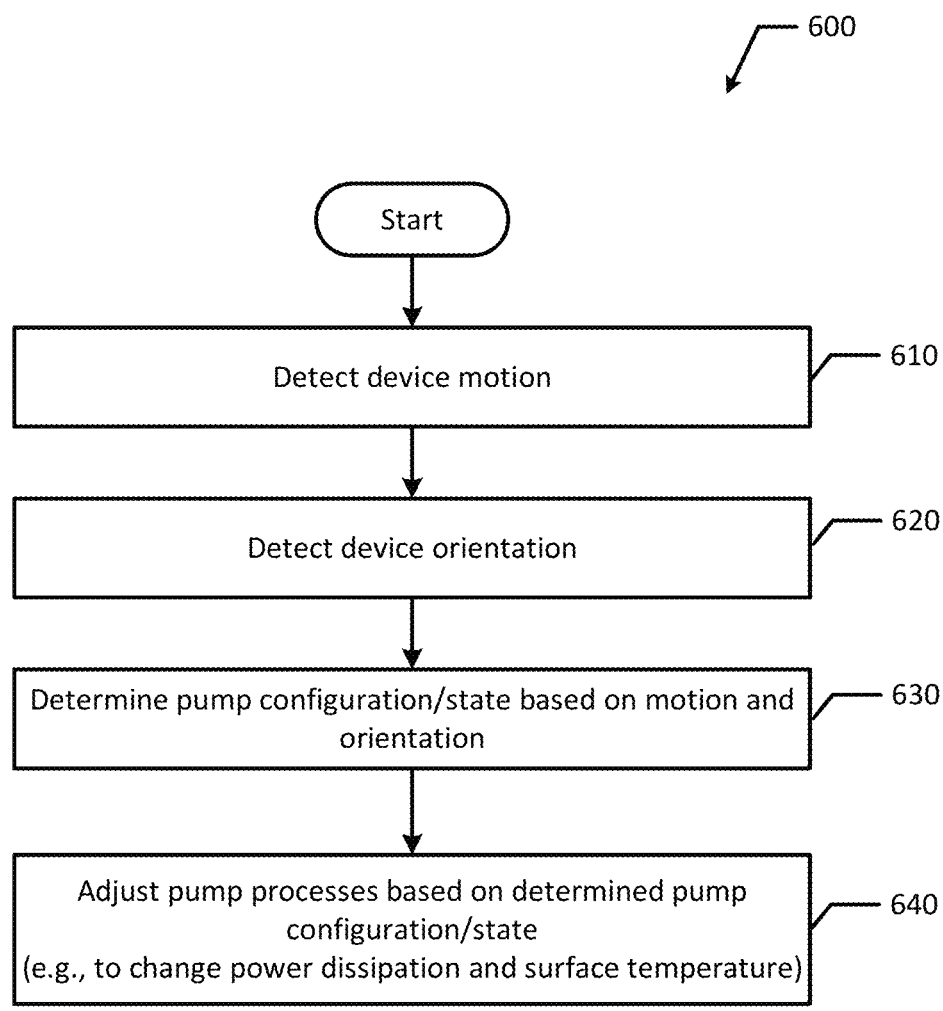
FIG. 6 is a flow chart of an example process for adjusting pump power dissipation based on the pump configuration according to an example embodiment of the present disclosure.

FIG. 6 illustrates a method of adjusting pump power dissipation based on pump configuration. At block 610, an accelerometer detects device motion. For example, the accelerometer may detect acceleration data (e.g., "g-values") of the pump 110 in the x-direction, y-direction and z-direction. The detected motion (e.g., magnitude of the "g-values") may form part of the pump's accelerometer "signature". At block 620, the accelerometer detects device orientation. For example, the accelerometer may detect the pump's angular orientation. The detected angular orientation may form part of the pump's accelerometer "signature". At block 630, a controller determines a use scenario based on the motion and orientation. For example, a temperature control unit 230 may determine a use scenario based on the accelerometer "signature", which includes readings of motion and angular orientation. The "signature" may be compared to certain detection criteria (e.g., above an instantaneous threshold, above a cumulative threshold, according to a configuration prediction function). Based on the comparison, the pump 110 may be classified as being in either an ambulatory configuration or a non-ambulatory configuration. In an example, the detection criteria or configuration prediction algorithm may ensure that the pump 110 is properly classified such that the appropriate threshold for the pump's external housing temperature may be established. At block 640, the controller adjusts pump parameters according to a surface temperature threshold. The temperature control unit 230 may adjust power consumption by changing settings of the following pump functions or features: pump communication, battery charging, display (e.g., brightness and time-out), sounds and alerts, USB, WiFi communication frequency, CPU rate, CPU loading, etc.

Figure 7:
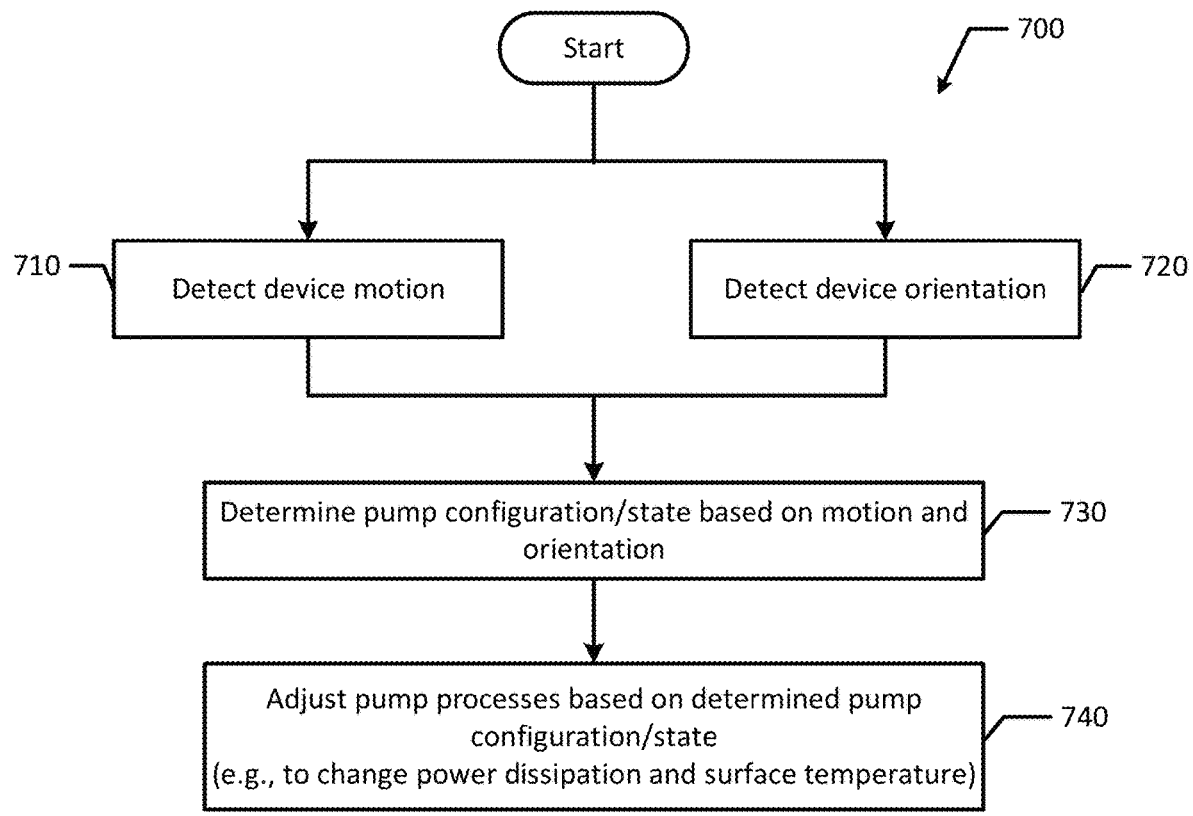
FIG. 7 is an example flow chart of an example process for adjusting pump power dissipation based on the pump configuration.

FIG. 7 illustrates a method of adjusting pump power dissipation based on pump configuration. At block 710, an accelerometer detects device motion. For example, the accelerometer may detect acceleration data (e.g., "g-values") of the pump 110 in the x-direction, y-direction and z-direction. The detected motion (e.g., magnitude of the "g-values") may form part of the pump's accelerometer "signature". At block 720, the accelerometer detects device orientation. For example, the accelerometer may detect the pump's angular orientation. The detected angular orientation may form part of the pump's accelerometer "signature". At block 730, a controller determines a use scenario based on at least one of the motion and orientation. For example, a temperature control unit 230 may determine a use scenario based on the accelerometer "signature", which includes readings of motion and angular orientation. The "signature" may be compared to certain detection criteria (e.g., above an instantaneous threshold, above a cumulative threshold, according to a configuration prediction function). Based on the comparison, the pump 110 may be classified as being in either an ambulatory configuration or a non-ambulatory configuration. In an example, the detection criteria or configuration prediction algorithm may ensure that the pump 110 is properly classified such that the appropriate threshold for the pump's external housing temperature may be established. At block 740, the controller adjusts pump parameters according to a surface temperature threshold. The temperature control unit 230 may adjust power consumption by changing settings of the following pump functions or features: pump communication, battery charging, display (e.g., brightness and time-out), sounds and alerts, USB, WiFi communication frequency, CPU rate, CPU loading, etc.

The many features and advantages of the present disclosure are apparent from the written description, and thus, the appended claims are intended to cover all such features and advantages of the disclosure. Further, since numerous modifications and changes will readily occur to those skilled in the art, the present disclosure is not limited to the exact construction and operation as illustrated and described. Therefore, the described embodiments should be taken as illustrative and not restrictive, and the disclosure should not be limited to the details given herein but should be defined by the following claims and their full scope of equivalents, whether foreseeable or unforeseeable now or in the future.

The invention claimed is:

1. An infusion pump comprising:
   a housing;
   a pumping mechanism;
   an accelerometer configured to detect pump motion and to output corresponding accelerometer data; and
   a temperature control unit, wherein the temperature control unit:
   receives the accelerometer data,
   determines a pump angular orientation based on the g-values of the accelerometer data,
   determines a pump configuration based on the pump angular orientation, the pump configuration including one of a contact configuration corresponding to relatively greater changes to the pump angular orientation and a non-contact configuration corresponding to relatively less changes to the pump angular orientation,
   establishes a threshold housing temperature based on the determined pump configuration, and
   maintains a temperature of the housing below the threshold housing temperature by modifying at least one pump feature or function, the at least one pump feature or function based on the determined pump configuration, feedback information from the temperature control unit, and ambient temperature information from the temperature control unit.

2. The infusion pump of claim 1, further comprising one or more temperature sensors.

3. The infusion pump of claim 2, wherein the temperature control unit is further configured to receive temperature data from the one or more temperature sensors.

4. The infusion pump of claim 3, wherein the temperature control unit is further configured to dynamically modify the at least one pump feature or function based on feedback from the temperature data.

5. The infusion pump of claim 1, wherein the contact configuration is an ambulatory configuration.

6. The infusion pump of claim 1, wherein the non-contact configuration is a non-ambulatory configuration.

7. The infusion pump of claim 1, wherein the pump is an ambulatory infusion pump.

8. The infusion pump of claim 1, wherein the infusion pump is connected to an I.V. pole when in the non-contact configuration.

9. The infusion pump of claim 1, wherein the at least one pump feature or function includes at least one of pump communication settings, battery charging settings, display settings, sound settings, alert settings, or WiFi communication frequency.

10. A method comprising:
    a temperature control unit, wherein the temperature control unit: receives accelerometer data,
    determines a pump angular orientation based on the g-values of the accelerometer data,
    determines a pump configuration based on the pump angular orientation, the pump configuration including one of a contact configuration and a non-contact configuration;
    establishes a threshold housing temperature based on the determined pump configuration, and
    maintains a temperature of the housing below the threshold housing temperature by modifying at least one pump feature or function, the at least one pump feature or function based on the determined pump configuration, feedback information from the temperature control unit, and ambient temperature information from the temperature control unit.

11. The method of claim 10, further comprising setting the threshold housing temperature.

12. The method of claim 10, wherein determining the pump configuration includes comparing the accelerometer data to a pre-established pump profile or pump signature.

13. The method of claim 10, wherein determining the pump configuration includes comparing the accelerometer data to an instantaneous threshold value.

14. The method of claim 10, wherein determining the pump configuration includes comparing the accelerometer data to a cumulative threshold value.

15. The method of claim 10, wherein determining the pump configuration includes applying the accelerometer data to a configuration prediction function.

16. The method of claim 10, wherein the at least one pump feature or function includes pump communication settings, battery charging settings, display settings, sound settings, alert settings, and WiFi communication frequency.

17. A method comprising:
    a temperature control unit, wherein the temperature control unit:
    detects a device motion and a device orientation;
    determines a device configuration based on the device motion and the device orientation; and
    modifies at least one pump feature and or function of a pumping mechanism to maintain a temperature of a device housing below a threshold housing temperature based on the determined device configuration, the at least one pump feature or function based on the determined pump configuration, feedback information from the temperature control unit, and ambient temperature information from the temperature control unit.

18. The method of claim 17, wherein the device is an infusion pump.

19. The method of claim 18, wherein the infusion pump is an ambulatory infusion pump.

20. The method of claim 17, wherein adjusting device processes includes at least one of adjusting device communication settings, adjusting battery recharge rate, adjusting display brightness, adjusting display time-out, adjusting speaker settings, adjusting alert frequency, and adjusting WiFi communication frequency.

\* \* \* \* \*